United States Patent
Old et al.

(10) Patent No.: US 7,015,243 B2
(45) Date of Patent: Mar. 21, 2006

(54) CYCLOHEXYL PROSTAGLANDIN ANALOGS AS EP$_4$-RECEPTOR AGONISTS

(75) Inventors: David W. Old, Irvine, CA (US); Robert M. Burk, Laguna Beach, CA (US); Thang D. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/652,634

(22) Filed: Aug. 28, 2003

(65) Prior Publication Data

US 2005/0049227 A1     Mar. 3, 2005

(51) Int. Cl.
*A61K 31/38*     (2006.01)
*C07D 327/04*    (2006.01)

(52) U.S. Cl. ..................... 514/443; 514/529; 549/32; 560/8; 560/129

(58) Field of Classification Search ................ 514/529, 514/443; 560/8, 129; 549/32
See application file for complete search history.

(56) References Cited

U.S. PATENT DOCUMENTS

| | | | |
|---|---|---|---|
| 3,985,798 A | 10/1976 | Floyd, Jr. et al. | |
| 4,060,540 A | 11/1977 | Bernady et al. | |
| 4,994,274 A | 2/1991 | Chan et al. | |
| 5,028,624 A | 7/1991 | Chan et al. | |
| 5,034,413 A | 7/1991 | Chan et al. | |
| 5,446,041 A | 8/1995 | Chan et al. | |
| 6,531,614 B1 * | 3/2003 | Conrow ..................... 549/214 | |

OTHER PUBLICATIONS

Brawner et al, "Prostaglandins and congeners. 21. Synthesis of some cyclohexyl analogs", XP002310257, Journal of Organic Chemistry, 44(1), 71-5, 1979.
Lopez-Pelegrin et al, "Solution-and soluble-polymer supported asymmetric synthesis of six-membered ring prostanoids", SP002310258, Chemistry-A European Journal, 6(11) 1917-1922, 2000.
Ohuchida et al, "Synthesis of thromboxane A2 analogs-3. (+)-Thiathromboxane A2", XP002310259, Tetrahedron, 39(24), 4269-72, 1983.
Crossley et al, "Cyclohexane analogs of the prostaglandins", XP002310260, Tetrahedron Letters, (36), 3327-30, 1971.
Bito, L.Z., *Biological Protection with Prostaglandins*, "Prostaglandins and Related Compounds as Potential Ocular Therapeutic Agents", vol. 1, Chapter 18, 1985, pp. 231-252.
Bito, L.Z., *Glaucoma, Applied Pharmacology in the Medical Treatment*, "Prostaglandins, Other Eicosanoids, and Their Derivatives as Potential Antiglaucoma Agents",1984, Chapter 20, pp. 477-505.
Nilsson et al, Invest. Ophthalmol. Vis. Sci. (suppl), 284 (1987), Arvo Abstracts 9-6:00.
Bito, L.Z., Arch. Ophthalmol. "Prostaglandins" "Old Concepts and New Perspectives", vol. 105, pp. 1036-1039 (1987).
Siebold et al, Prodrug 5 3, "Esterified protaglandin shows 'potent' promise",1989.
Lopez-Pelegrin et al, "Solution- and Soluble-Polymer Supported Asymmetric Synthesis of Six-Membered Ring Prostanoids", Chem. Eur. J. 2000, 6, 1917-1922.
Hareau et al, "Synthesis of Optically Active 5-(tert-Butyldimethylsiloxy)-2-cyclohexenone and Its 6-Substituted Derivatives as Useful Chiral Building Blocks for the Synthesis of Cyclohexane Rings. Syntheses of Carvone, Penienone, and Penihydrone", J. Am. Chem. Soc. 1999, 121, 3640-3650.

* cited by examiner

Primary Examiner—Taofiq Solola
Assistant Examiner—Robert Shiao
(74) *Attorney, Agent, or Firm*—Brent A. Johnson; Martin A. Voet; Robert J. Baran (57) ABSTRACT

The invention relates to the use of novel cyclohexyl analogues of E-type prostaglandins as EP$_4$ agonists, in general, and, in particular as ocular hypotensives. The cyclohexyl analogues used in accordance with the invention are represented by the following formula I:

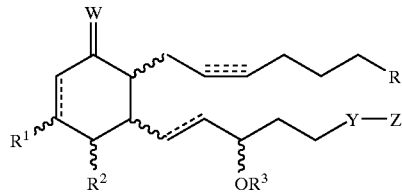

wherein the wavy segments represent α or β bond, dashed line represents the presence or absence of a bond W, Y, Z, R, $R^1$, $R^2$ and $R^3$ are as defined in the specification.

6 Claims, 6 Drawing Sheets

CYCLOHEXYL PROSTAGLANDIN ANALOGS AS EP$_4$-RECEPTOR AGONISTS

BACKGROUND OF THE INVENTION

1. Field of the Invention

The present invention relates to cyclohexyl prostaglandin analogs as EP$_4$-receptor agonists. These compounds are potent ocular hypotensives and are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin E$_1$ (PGE$_1$), prostaglandin E$_2$ (PGE$_2$)], and on the configuration of the substituents on the alicyclic ring indicated by α or β [[e.g. prostaglandin F$_{2\alpha}$ (PGF$_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include PGF$_{2\alpha}$, PGF$_{1\alpha}$, PGE$_2$, and certain lipid-soluble esters, such as C$_1$ to C$_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of PGF$_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et. al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF$_{2\square}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed 10 Oct. 1990), now U.S. Pat. 5,446,041, relates to certain 11-acyl-prostaglandins, such as 11-pivaloyl, 11-acetyl, 11-isobutyryl, 11-valeryl, and 11-isovaleryl PGF$_{2\alpha}$. Intraocular pressure reducing 15-acyl prostaglandins are disclosed in the co-pending application U.S. Ser. No. 175,476 (filed 29 Dec. 1993, now abandoned). Similarly, 11,15-9,15 and 9,11-diesters of prostaglandins, for example 11,15-dipivaloyl PGF$_{2\alpha}$ are known to have ocular hypotensive activity. See the co-pending patent applications U.S. Ser. Nos. 385,645 (filed 07 Jul. 1989, now U.S. Pat. No. 4,994,274), 584,370

(filed 18 Sep. 1990, now U.S. Pat. No. 5,028,624) and 585,284 (filed 18 Sep. 1990, now U.S. Pat. No. 5,034,413). The disclosures of all of these patent applications are hereby expressly incorporated by reference.

SUMMARY OF THE INVENTION

The present invention concerns a method of treating ocular hypertension and/or glaucoma which comprises administering to a mammal having ocular hypertension and/or glaucoma a therapeutically effective amount of a compound of formula I wherein the wavy segment represents α or β bond, a dashed line represents the presence or absence of a bond, R is selected from the group consisting of $CO_2R^4$, $CONR^4{}_2$, $CH_2OR^4$, $CONR^4SO_2R^4$, $P(O)(OR^4)$ and wherein $R^4$ is selected from the group consisting of H, phenyl and lower alkyl having from one to six carbon atoms and n is 0 or an integer of from 1 to 4, $R^1$ and $R^2$ are independently selected from the group consisting of hydrogen, hydroxyl, a lower alkyloxy radical having up to six carbon atoms, or a lower acyloxy radical having up to six carbon atoms, $R^3$ is selected from the group consisting of hydrogen, a lower alkyl radical having up to six carbon atoms and a lower acyl radical having up to six carbon atoms, W is =O or halogen, Y is a covalent bond or is selected from the group consisting of $CH_2$, O, S and N and Z is a alkyl or cycloalkyl radical including from three to ten carbon atoms or an aromatic radical including a hydrocarbyl aromatic radical having from six to ten carbon atoms or a heterocyclic aromatic radical having from four to ten carbon atoms and including a heterocyclic atom selected from the group consisting of nitrogen, oxygen and sulfur; and pharmaceutically-acceptable salts and esters thereof.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising
  a container adapted to dispense its contents in a metered form; and
  an ophthalmic solution therein, as hereinabove defined.

Finally, certain of the compounds represented by the above formula, disclosed below and utilized in the method of the present invention are novel and unobvious.

DETAILED DESCRIPTION OF THE INVENTION

The present invention relates to the use of cyclohexyl prostaglandin analogs as $EP_4$-receptor agonists. The compounds used in accordance with the present invention are encompassed by the following structural formula I:

wherein the wavy segment represents α or β bond, a dashed line represents the presence or absence of a bond, R is selected from the group consisting of $CO_2R^4$, $CONR^4{}_2$, $CH_2OR^4$, $CONR^4SO_2R^4$, $P(O)(OR^4)$ and wherein $R^4$ is selected from the group consisting of H, phenyl and lower alkyl having from one to six carbon atoms and n is 0 or an integer of from 1 to 4. $R^1$ and $R^2$ are independently selected from the group consisting of hydrogen, hydroxyl, a lower alkyloxy radical having up to six carbon atoms, or a lower acyloxy radical having up to six carbon atoms, $R^3$ is selected from the group consisting of hydrogen, a lower alkyl radical having up to six carbon atoms and a lower acyl radical having up to six carbon atoms, W is =O or halogen, Y is a covalent bond or is selected from the group consisting of CH$_2$, O, S and N and Z is a alkyl or cycloalkyl radical including from three to ten carbon atoms or an aromatic radical including a hydrocarbyl aromatic radical having from six to ten carbon atoms or a heterocyclic aromatic radical having from four to ten carbon atoms and including a heterocyclic atom selected from the group consisting of nitrogen, oxygen and sulfur; and pharmaceutically-acceptable salts and esters thereof.

A preferred group of the compounds of the present invention includes compounds that have the following structural formula II:

wherein the hatched segment represents an α bond and the solid triangle represents a β bond.

Another preferred group includes compounds having the formula III:

The most preferred group of compounds utilized in the method of the present invention are selected from the group wherein Z is phenyl or represented by the formula IV wherein U is selected from the group consisting of O and S, A is selected from the group consisting of N, —CH and C, R$^5$ is selected from the group consisting of hydrogen, halogen, lower alkyl having from 1 to 6 carbon atoms and lower alkoxy having from 1 to 6 carbon atoms, R$^6$ and R$^7$ are selected from the group consisting of hydrogen, halogen, lower alkyl having from 1 to 6 carbon atoms and lower alkoxy having from 1 to 6 carbon atoms, or, together with R$^6$ and R$^7$ forms a condensed aryl ring.

Preferably R is CO$_2$R$^4$ and more preferably R$^4$ is H or methyl.

The above compounds of the present invention may be prepared by methods that are known in the art or according to the working examples below. The compounds, below, are especially preferred representative of the compounds of the present invention.

(Z)-7-{(1R,2R)-2-[(E)-5-(3-Chloro-benzo[b]thiophen-2-yl)-3-hydroxy-pent-1-enyl]-6-oxo-cyclohexyl}-hept-5-enoic acid (Z)-7-{(1R,6R)-6-[(E)-5-(3-Chloro-benzo[b]thiophen-2-yl)-3-hydroxy-pent-1-enyl]-2-oxo-cyclohex-3-enyl}-hept-5-enoic acid 7-[(1R,2R,3R)-3-Hydroxy-2-((S)-3-hydroxy-octyl)-6-oxo-cyclohexyl]-heptanoic acid 7-[(1R,2R,3R)-3-Hydroxy-2-((E)-3-hydroxy-5-phenyl-pent-1-enyl)-6-oxo-cyclohexyl]-hept-5-ynoic acid (Z)-7-{(1R,2R,3R)-2-[(E)-5-(3-Chloro-benzo[b]thiophen-2-yl)-3-hydroxy-pent-1-enyl]-3-hydroxy-6-oxo-cyclohexyl}-hept-5-enoic acid (Z)-7-[(1R,2R,3R)-3-Hydroxy-2-((E)-3-hydroxy-4-phenyl-but-1-enyl)-6-oxo-cyclohexyl]-hept-5-enoic acid 7-[(1R,2R,3R)-2-((E)-4-Benzo[b]thiophen-3-yl-3-hydroxy-but-1-enyl)-3-hydroxy-6-oxo-cyclohexyl]-hept-5-ynoic acid (Z)-7-[(1R,2R,3R)-2-((E)-4-Benzo[b]thiophen-3-yl-3-hydroxy-but-1-enyl)-3-hydroxy-6-oxo-cyclohexyl]-hept-5-enoic acid (Z)-7-[(1R,2R,4S)-4-Hydroxy-2-((E)-3-hydroxy-4-phenyl-but-1-enyl)-6-oxo-cyclohexyl]-hept-5-enoic acid (Z)-7-{(1R,2R,3R,6R)-6-Chloro-2-[(E)-5-(3-chloro-benzo[b]thiophen-2-yl)-3-hydroxy-pent-1-enyl]-3-hydroxy-cyclohexyl}-hept-5-enoic acid A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 1:
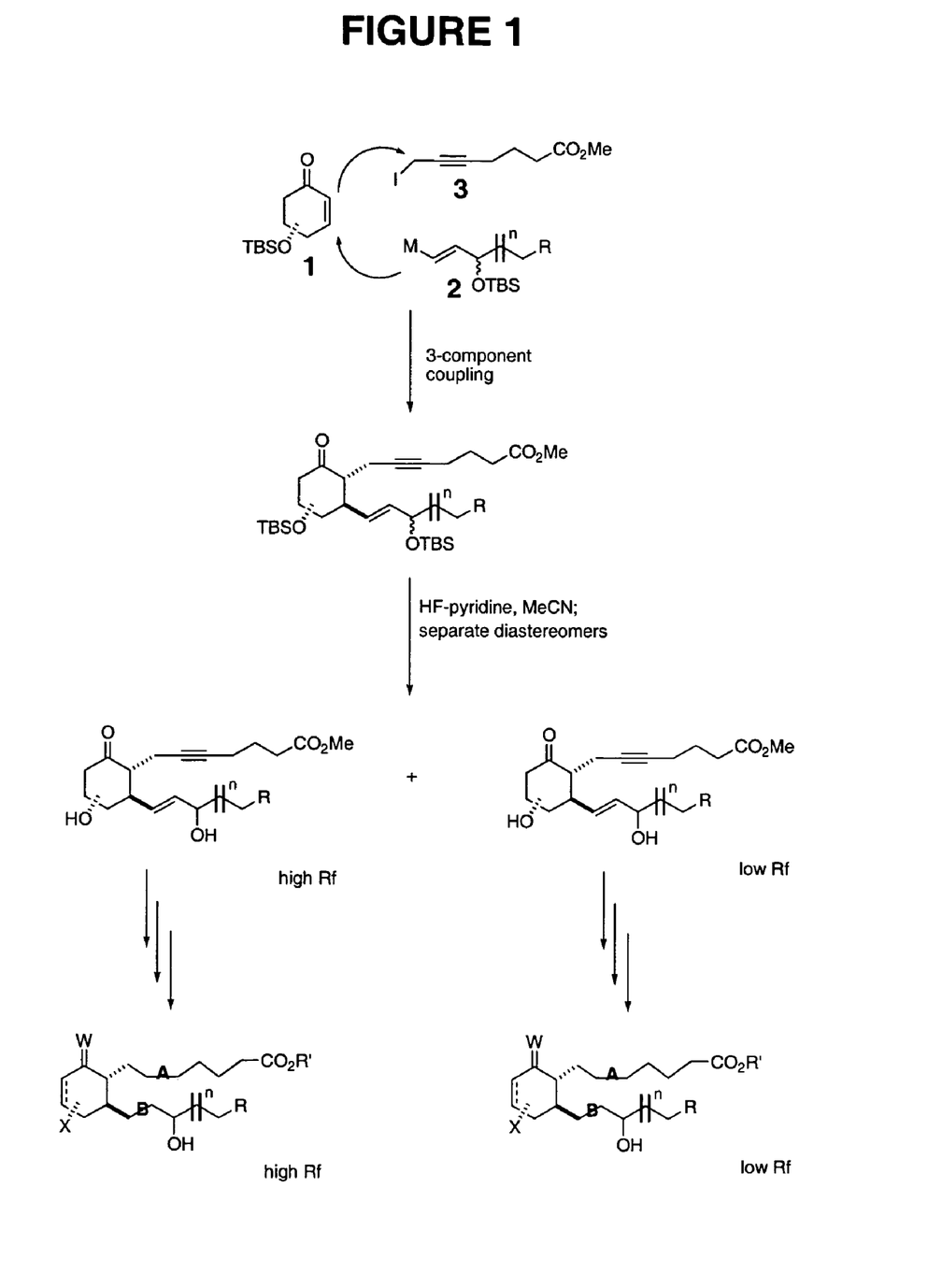
FIG. 1 is a schematic of a general chemical synthesis of preparing compounds of the invention including those having an alpha chain that includes a double or triple bond.
Figure 2:
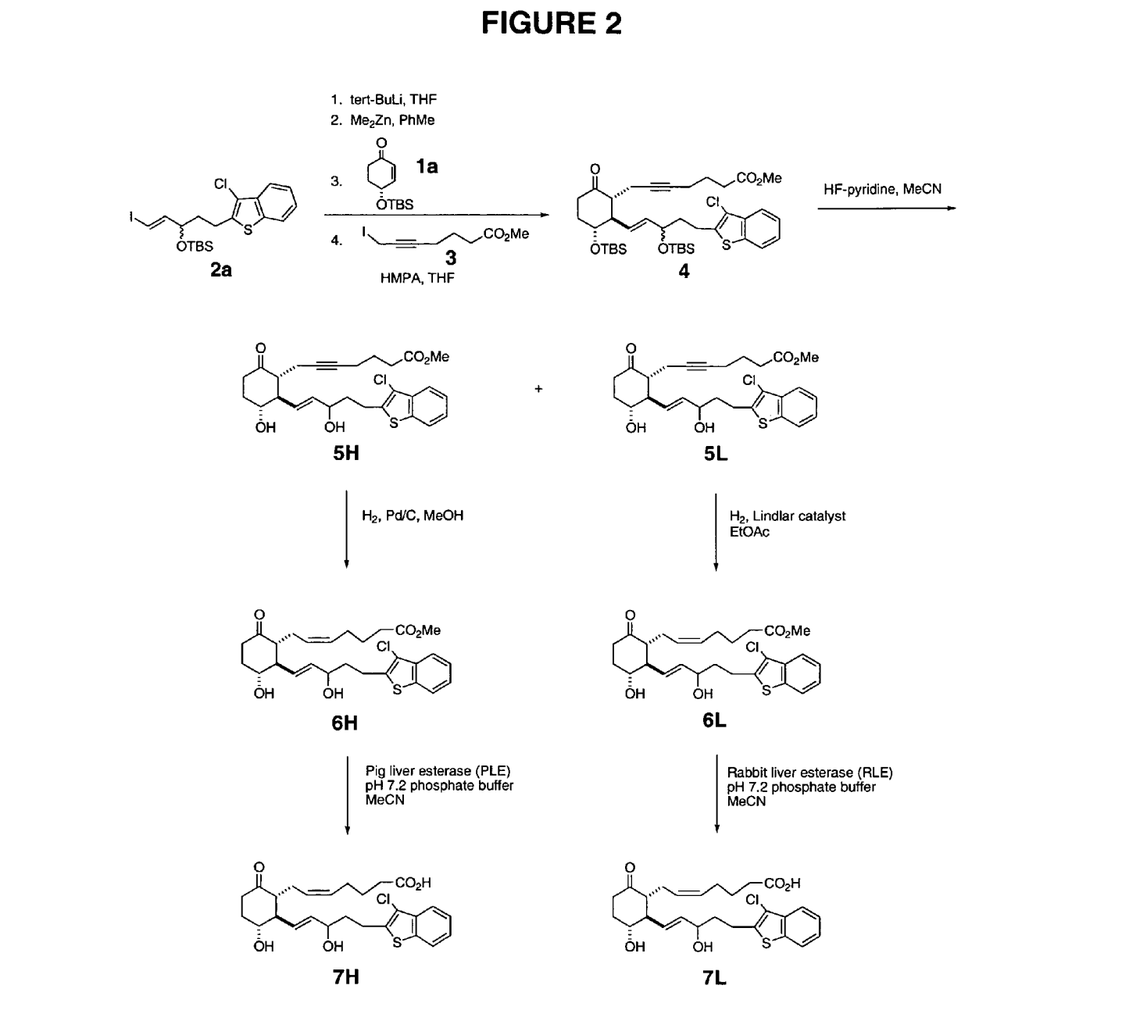
FIG. 2 is a schematic of the chemical synthesis of certain compounds of the invention specifically disclosed as Example 1.

The invention is further illustrated by the following non-limiting Examples, which are summarized in the reaction schemes of FIGS. 1 and 2, wherein the compounds are identified by the same designator in both the Examples and the Figures.

EXAMPLE 1

(Z)-7-{(1R,2R,3R)-2-[(E)-5-(3-Chloro-benzo[b]thiophen-2-yl)-3-hydroxy-pent-1-enyl]-3-hydroxy-6-oxo-cyclohexyl}-hept-5-enoic acid (7H and 7L, FIG. 2)

Step 1. Three component coupling of 1a, 2a and 3 to give 4.

tert-Butyl lithium (1.7 M in pentane, 1.93 mL, 3.3 mmol) was added to a solution of {(E)-1-[2-(3-chloro-benzo[b]thiophen-2-yl)-ethyl]-3-iodo-allyloxy}-tert-butyldimethyl-silane (2a, 740 mg, 1.5 mmol) in THF (3.0 mL) at −78° C. under nitrogen. (2a was prepared as disclosed in U.S. patent application Ser. No. 365,369 which was filed on Feb. 11, 2003 and is hereby incorporated by reference.) After 15 min at −78° C., dimethylzinc (2.0 M in PhMe, 0.73 mL, 1.5 mmol) was added and the reaction solution was warmed to 0° C. After 15 min at 0° C. the reaction was recooled to −78° C. A solution of enone 1a (226 mg, 1.0 mmol) in THF (1.0 mL) was added over 50 min via syringe pump, rinsing the syringe with THF (0.5 mL). 1a was prepared as disclosed in (López-Pelegrín, J. A.; Janda, K. D. Chem. Eur. J. 2000, 6, 1917–1922 and references therein.) After 15 min, HMPA (1.74 mL, 10.0 mmol) was added. After an additional 15 min, a solution of propargyl iodide 3 (1.33 g, 5.0 mmol) in THF (3.0 mL) was added. (3 was prepared from the corresponding propargylic alcohol [Casy, G.; Petersen, J. W.; Taylor, R. J. K. Org. Synth. 1993, Collect. Vol. VIII, 415–420] using iodine, triphenylphosphine and imidazole in dichloromethane solvent.)

The reaction was then placed into a cryobath at −40° C. and maintained at that temperature for 21 h. The reaction was quenched with saturated aqueous NH$_4$Cl (40 mL) and extracted with EtOAc (3×25 mL). The combined organic phases were washed with brine (50 mL), dried (Na$_2$SO$_4$), filtered and concentrated in vacuo. Purification of the resulting residue by flash column chromatography on silica gel (0→7% EtOAc/Hex, gradient) afforded 335 mg (46%) of desired product 4.

Step 2. Deprotection to give 5H and 5L.

HF-pyridine (0.6 mL) was added to a solution of the bis-silyl ether from step 1 (4, 150 mg, 0.21 mmol) in MeCN (4.0 mL) in a plastic scintillation vial. After stirring overnight at rt, the reaction was quenched with saturated aqueous NaHCO$_3$ (20 mL) and extracted with EtOAc (3×25 mL). The organic phase was washed with brine (10 mL), dried (Na$_2$SO$_4$), filtered and concentrated in vacuo. Purification of the resulting (50→100% EtOAc/Hex, gradient) afforded 29.2 mg (28%) of the high Rf diastereomer (5H) and 26.5 mg (26%) of the low Rf diastereomer (5L).

Step 3. Reduction of alkyne to give alkene 6H and 6L.

Method A. Pd/C (10 mol %, 2 mg) was added to a solution of the high Rf alkyne from step 2 (5H, 6.0 mg, 0.012 mmol) in MeOH (1.5 mL). A hydrogen atmosphere was established by evacuating and refilling with hydrogen (3×) and the reaction mixture was stirred under a balloon of hydrogen for 1.25 h. The reaction mixture was filtered through celite and the filtrate was concentrated in vacuo. Purification of the resulting residue by preparative thin layer chromatography (silica, 100% EtOAc) afforded 4.6 mg (76%) of 6H with 1.0 mg of recovered 5H.

Method B. Lindlar catalyst (20 mg) was added to a solution of the low Rf alkyne from step 2 (5L, 20 mg, 0.04 mmol) in EtOAc (2.0 mL). A hydrogen atmosphere was established by evacuating and refilling with hydrogen (3×) and the reaction mixture was stirred under a balloon of hydrogen for 19 h. The reaction mixture was filtered through celite, washing with EtOAc, and the filtrate was concentrated in vacuo. Purification of the resulting residue by preparative thin layer chromatography (silica, 100% EtOAc) afforded 4.8 mg (24%) of 6L along with 10 mg of recovered 5L.

Step 4. Conversion of ester to acid 7H and 7L.

Method A. A solution of the ester from step 3A (6H, 2.6 mg, 0.005 mmol), MeCN (0.1 mL), pH 7.2 phosphate buffer (2.0 mL) and pig liver esterase (50 μL) were stirred together overnight at rt. The mixture was extracted with EtOAc (2×10 mL). The combined extracts were washed with brine (10 mL), dried (Na$_2$SO$_4$), filtered and concentrated in vacuo to afford 2.0 mg (79%) of the title compound (7H).

Method B. A solution of the ester from step 3B (6L, 3 mg, 0.006 mmol), MeCN (0.1 mL), pH 7.2 phosphate buffer (3.0 mL) and rabbit liver esterase (1 mg) were stirred together overnight at rt. The mixture was concentrated in vacuo to dryness. Purification of the resulting residue by preparative thin layer chromatography (silica, 10% MeOH/CH$_2$Cl$_2$) afforded 0.8 mg (27%) of the title compound (7L).

EXAMPLE 2

(Z)-7-[(1R,2R,3R)-3-Hydroxy-2-((E)-3-hydroxy-4-phenyl-but-1-enyl)-6-oxo-cyclohexyl]-hept-5-enoic acid Prepared from ((E)-1-Benzyl-3-iodo-allyloxy)-tert-butyldimethylsilane (2b) and enone 1a in accordance with the procedures in Example 1 (steps 1, 2, 3B and 4B). (2b was prepared analogously to 2a, above.)

EXAMPLE 3

(Z)-7-[(1R,2R,3R)-2-((E)-4-Benzo[b]thiophen-3-yl-3-hydroxy-but-1-enyl)-3-hydroxy-6-oxo-cyclohexyl]-hept-5-enoic acid Prepared from ((E)-1-Benzo[b]thiophen-3-ylmethyl-3-iodo-allyloxy)-tert-butyldimethylsilane (2c) and enone 1a in accordance with the procedures in Example 1 (steps 1, 2 and 4B) and 3C (see below). (2c was prepared analogously to 2a, above.)

Step 3. Reduction of alkyne to give alkene.

Method C. Sodium borohydride (8.0 mg, 0.21 mmol) was added to a suspension of nickel (II) chloride (55 mg, 0.43 mmol) in 95% ethanol (2.0 mL) and the mixture immediately turned black. After 5 min at rt, ethylenediamine (46 μL, 0.69 mmol) was added. After 15 min at rt, the alkyne from step 2 (40 mg, 0.085 mmol) was added in 95% ethanol (2.0 mL). A hydrogen atmosphere was established by evacuating and refilling with hydrogen (3×) and the reaction mixture was stirred under a balloon of hydrogen for 19 h. The reaction mixture was filtered through celite, washing with ethanol, and the filtrate was concentrated in vacuo. Purification of the resulting residue by flash column chromatography (50→100% EtOAc/Hex, gradient) afforded 20 mg (50%) of the desired alkene.

EXAMPLE 4

7-[(1R,2R,3R)-3-Hydroxy-2-((E)-3-hydroxy-5-phenyl-pent-1-enyl)-6-oxo-cyclohexyl]-hept-5-ynoic acid Prepared from ((E)-3-iodo-1-phenethyl-allyloxy)-tert-butyldimethylsilane (2d) and enone 1a in accordance with the procedures in Example 1 (steps 1, 2 and 4B). (2d was prepared analogously to 2a, above.)

EXAMPLE 5

(Z)-7-[(1R,2R,4S)-4-Hydroxy-2-((E)-3-hydroxy-4-phenyl-but-1-enyl)-6-oxo-cyclohexyl]-hept-5-enoic acid Prepared from (2b) and (S)-5-(tert-butyldimethylsiloxy)-2-cyclohexenone (1b) in accordance with the procedures in Examples 1 and 3 (steps 1, 2, 3C and 4B). (1b was prepared as described in Hareau, G. P-J. et. al.; J. Am. Chem. Soc. 1999, 121, 3640–50.)

EXAMPLE 6

Figure 3:
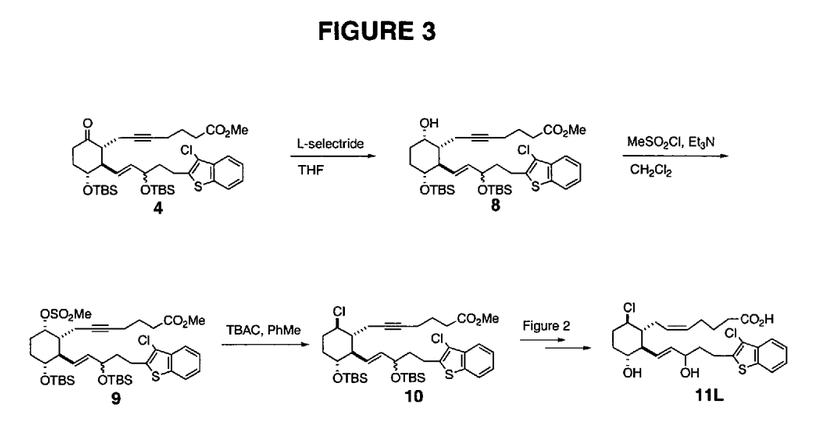
FIG. 3 is a schematic of the chemical synthesis of certain compounds of the invention specifically disclosed as Example 6.

(Z)-7-{(1R,2R,3R,6R)-6-Chloro-2-[(E)-5-(3-chloro-benzo[b]thiophen-2-yl)-3-hydroxy-pent-1-enyl]-3-hydroxy-cyclohexyl}-hept-5-enoic acid (11L, FIG. 3)

Step 1. Conversion of ketone 4 to α-alcohol 8.

L-selectride (1.0 M in THF, 0.76 mL, 0.76 mmol) was added to a solution of the product of Example 1, step 1 (4, 370 mg, 0.51 mmol) in THF (5.0 mL) at −78° C. under nitrogen. After 30 min, formic acid (0.4 ml) was added and the reaction was allowed to warm to 0° C. After 30 min, aqueous HCl (1.0 M, 5 mL) was added and the mixture was extracted with EtOAc (3×30 mL). The combined organic phase was washed with brine then dried (Na$_2$SO$_4$), filtered and concentrated in vacuo. Purification of the resulting residue by flash column chromatography on silica gel (10→15% EtOAc/Hex, gradient) afforded 194 mg (53%) of 8.

Step 2. Conversion of alcohol 8 to mesylate 9.

Methanesulfonyl chloride (24 μL, 0.31 mmol) and triethylamine (54 μL, 0.39 mmol) were added sequentially to a solution of the alcohol from step 1 (8, 188 mg, 0.26 mmol) in CH$_2$Cl$_2$ (2.0 mL) at rt. After 5 h, an additional portion of methanesulfonyl chloride (40 μL, 0.51 mmol) and triethylamine (54 μL, 0.39 mmol) were added. After stirring overnight at rt, saturated aqueous NaHCO$_3$ (10 mL) was added and the reaction mixture was extracted with CH$_2$Cl$_2$ (3×15 mL). The combined organic phase was dried (Na$_2$SO$_4$), filtered and concentrated in vacuo. Purification of the resulting residue by flash column chromatography on silica gel (10→20% EtOAc/Hex, gradient) afforded 134 mg (64%) of 9.

Step 3. Conversion of α-mesylate 9 to β-chloride 10.

The mesylate from step 2 (9, 130 mg, 0.16 mmol), tetrabutylammonium chloride (445 mg, 1.6 mmol) and toluene (5.0 mL) were combined and stirred together at 40° C. under nitrogen overnight. The reaction was cooled to rt, brine (10 mL) was added, and the mixture was extracted with EtOAc (3×15 mL). The combined organic phase was dried (Na$_2$SO$_4$), filtered and concentrated in vacuo. Purification of the resulting residue by flash column chromatography on silica gel (10% EtOAc/Hex) afforded 31 mg (26%) of 10 along with 53 mg of recovered 9.

The product of step 3 was then converted to the title product (11) in accordance with the procedures in Examples 1 and 3 (steps 2, 3C and 4B).

EXAMPLE 7

Figure 4:
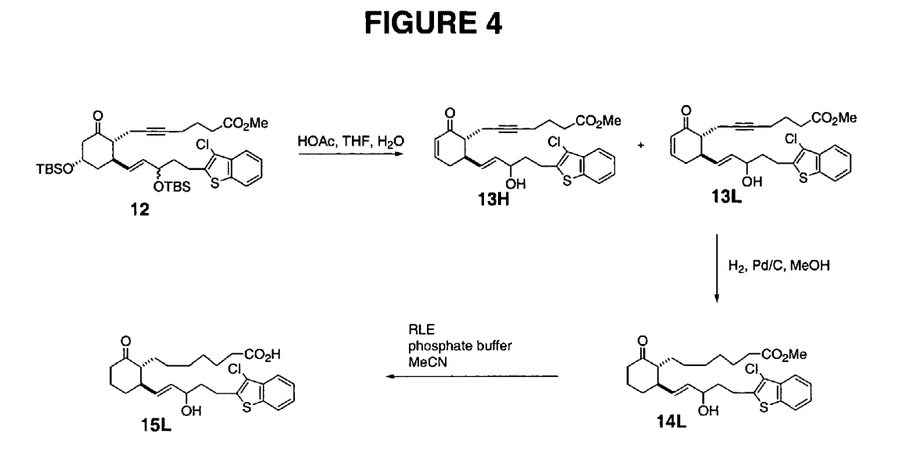
FIG. 4 is a schematic of the chemical synthesis of certain compounds of the invention specifically disclosed as Example 7.

(Z)-7-{(1R,2R)-2-[(E)-5-(3-Chloro-benzo[b]thiophen-2-yl)-3-hydroxy-pent-1-enyl]-6-oxo-cyclohexyl}-hept-5-enoic acid (15L, FIG. 4).

Step 1. Three component coupling of 1b, 2a and 3 to give 12.

The three component coupling product 12 was obtained from vinyl iodide 2a and enone 1b in accordance with the procedure in Example 1 (step 1).

Step 2. Deprotection and elimination to give 13H and 13L.

A mixture of the β-silyloxy ketone (12, 198 mg, 0.27 mmol) and acetic acid/THF/H$_2$O (2:1:1, 2.0 mL) was heated at 70° C. overnight. The reaction was cooled to rt, saturated aqueous NaHCO$_3$ (20 mL) was added and the mixture was extracted with EtOAc (2×20 mL). The combined organic phase was washed with brine (20 mL), dried (Na$_2$SO$_4$), filtered and concentrated in vacuo. $^1$H NMR analysis showed that the elimination reaction was incomplete, so the crude material was resubmitted to the reaction conditions for 3 d. The reaction was cooled to rt, saturated aqueous NaHCO$_3$ (15 mL) was added and the mixture was extracted with EtOAc (3×10 mL). The combined organic phase was dried (Na$_2$SO$_4$), filtered and concentrated in vacuo. Purification of the resulting residue by preparative thin layer chromatography (silica, 50% EtOAc/Hex) afforded 7.4 mg (6%) of 13H and 3.7 mg (3%) of 13L.

Step 3. Reduction to give 14L.

Pd/C (10 mol %, 1 mg) was added to a solution of the low Rf diastereomer from step 2 (13L, 3.7 mg, 0.0076 mmol) in MeOH (1.0 mL). A hydrogen atmosphere was established by evacuating and refilling with hydrogen (3×) and the reaction mixture was stirred under a balloon of hydrogen for 1 h. The reaction mixture was filtered through celite and the filtrate was concentrated in vacuo. Purification of the resulting residue by preparative thin layer chromatography (silica, 30% EtOAc/Hex) afforded 2.3 mg (61%) of 14L.

The product of step 3 was then converted to the title product 15L in accordance with the procedure in Example 1 (step 4B).

EXAMPLE 8

7-[(1R,2R,3R)-2-((E)-4-Benzo[b]thiophen-3-yl-3-hydroxy-but-1-enyl)-3-hydroxy-6-oxo-cyclohexyl]-hept-5-ynoic acid Prepared from vinyl iodide 2c and enone 1a in accordance with the procedures in Example 1 (steps 1, 2 and 4B).

EXAMPLE 9

Figure 5:
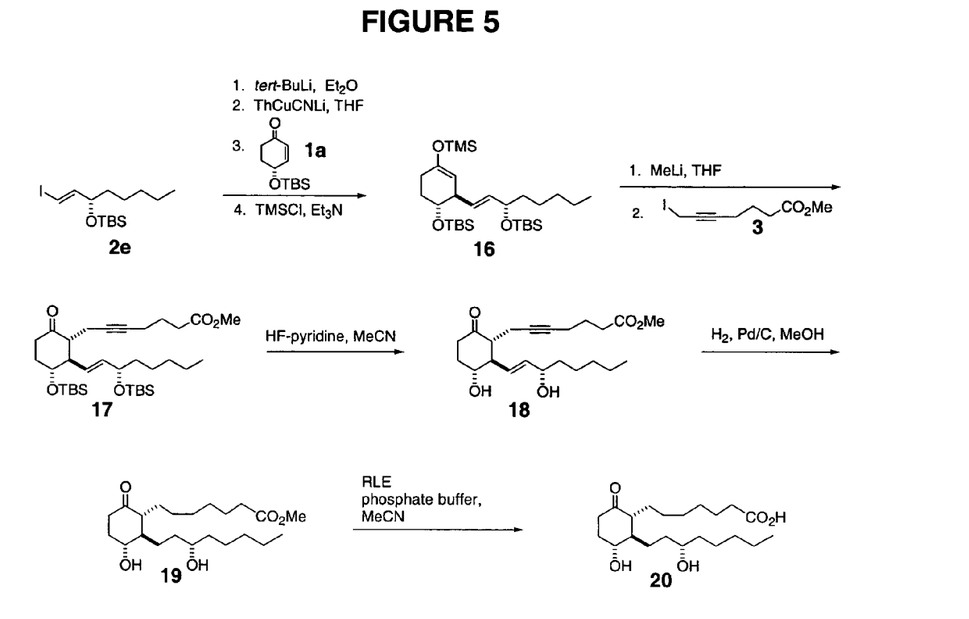
FIG. 5 is a schematic of the chemical synthesis of certain compounds of the invention specifically disclosed as Example 9.

7-[(1R,2R,3R)-3-Hydroxy-2-((S)-3-hydroxy-octyl)-6-oxo-cyclohexyl]-heptanoic acid (20, FIG. 5).

Step 1. Three component coupling to give 17 via enoxysilane 16.

A solution of [(S)-1-((E)-2-iodo-vinyl)-hexyloxy]-tert-butyldimethylsilane (2e, 500 mg, 1.36 mmol) in Et$_2$O (7.0 mL) at −78° C. under nitrogen was treated with tert-butyl lithium (1.7 M in pentane, 1.6 mL, 2.72 mmol). (2e was purchased from Nissan Chemical Industries.) After 30 min at −78° C., lithium 2-thienylcyanocuprate (0.25 M in THF, 5.44 mL, 1.36 mmol) was added. After 30 min at −78° C., a solution of enone 1a (237 mg, 1.05 mmol) in Et$_2$O (1.0 mL) was added dropwise. After 1.5 h min at −78° C., TMSCl (0.80 mL, 6.3 mmol) was added. After 15 min at −78° C., Et$_3$N (1.9 mL, 13.6 mmol) was added and the solution was allowed to warm to rt. The mixture was poured into hexanes and water. The phases were separated and the aqueous phase was extracted with additional hexanes (3×50 mL). The combined organic phases were dried (Na$_2$SO$_4$), filtered and concentrated in vacuo. A solution of crude enoxysilane 16 (~1.0 mmol) in THF (6.0 mL) at −23° C. under nitrogen was treated with methyl lithium (1.4 M in Et$_2$O, 1.1 mL, 1.5 mmol). After 30 min, the solution was cooled to −78° C. then a solution of iodide 3 (1.06 g, 4.0 mmol) in THF (7.0 mL) was added via cannula. After 1 h at −78° C., the reaction was warmed to −23° C. for 2 h then allowed to warm to rt. The reaction was quenched with saturated aqueous NH$_4$Cl (50 mL) and extracted with EtOAc (3×30 mL). The combined organic phases were washed with brine (75 mL), dried (Na$_2$SO$_4$), filtered and concentrated in vacuo. Purification of the resulting residue by flash column chromatography on silica gel (0→10% EtOAc/Hex) afforded 157 mg (25%) of 17.

Step 2. Deprotection to give 18.

HF-pyridine (0.3 mL) was added to a solution of the bis-silyl ether from step 1 (17, 150 mg, 0.25 mmol) in MeCN (3.0 mL) in a plastic scintillation vial. After stirring overnight at rt, the reaction was quenched with saturated aqueous NaHCO$_3$ (20 mL) and extracted with EtOAc (2×25 mL). The organic phase was washed with brine (25 mL), dried (Na$_2$SO$_4$), filtered and concentrated in vacuo. Purification of the resulting residue by flash column chromatography on silica gel (40→80% EtOAc/Hex, gradient) afforded 61 mg (65%) of 18.

Step 3. Reduction of the alkyne and the alkene to give 19.

Pd/C (10 mol %, 5 mg) was added to a solution of the product from step 2 (18, 15 mg, 0.039 mmol) in MeOH (1.5 mL). A hydrogen atmosphere was established by evacuating and refilling with hydrogen (3×) and the reaction mixture was stirred under a balloon of hydrogen overnight. The reaction mixture was filtered through celite and the filtrate was concentrated in vacuo. Purification of the resulting residue by flash column chromatography (30%→50% EtOAc/Hex, gradient) afforded 3.7 mg (25%) of 19.

Step 4. Conversion of ester to acid 20.

The product of step 3 was converted to the title product (20) in accordance with the procedure in Example 1 (step 4B).

EXAMPLE 10

Figure 6:
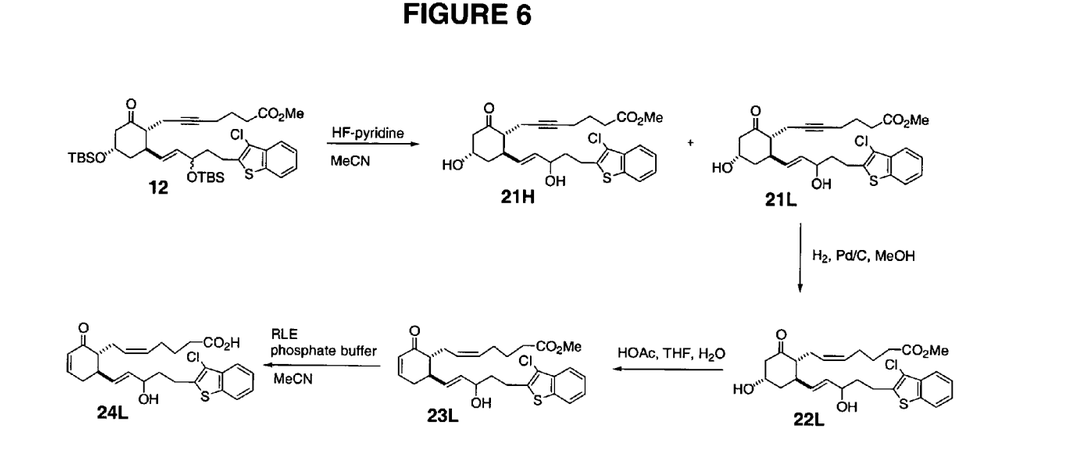
FIG. 6 is a schematic of the chemical synthesis of certain compounds of the invention specifically disclosed as Example 10.

(Z)-7-{(1R,6R)-6-[(E)-5-(3-Chloro-benzo[b]thiophen-2-yl)-3-hydroxy-pent-1-enyl]-2-oxo-cyclohex-3-enyl}-hept-5-enoic acid (24L, FIG. 6)

Step 1. Deprotection to give 21H and 21L.

HF-pyridine (1.5 mL) was added to a solution of the bis-silyl ether from Example 7, step 1 (12, 421 mg, 0.58 mmol) in MeCN (5.0 mL) in a plastic scintillation vial. After stirring 3 h at rt, the reaction was quenched with saturated aqueous NaHCO$_3$ (25 mL) and extracted with EtOAc (3×25 mL). The organic phase was washed with brine (25 mL), dried (Na$_2$SO$_4$) and concentrated in vacuo. Purification of the resulting residue by preparative thin layer chromatography (silica, 70% EtOAc/Hex) afforded 37 mg (13%) of 21H and 22 mg (8%) of 21L.

Step 2. Reduction of alkyne to alkene 22L.

Pd/C (10 mol %, 2 mg) was added to a solution of the product from step 1 (21L, 13 mg, 0.026 mmol) in MeOH (1.0 mL). A hydrogen atmosphere was established by evacuating and refilling with hydrogen (3×) and the reaction mixture was stirred under a balloon of hydrogen for 4.5 h. The reaction mixture was filtered through celite, washing with MeOH, and the filtrate was concentrated in vacuo. Purification of the resulting residue by preparative thin layer chromatography (silica, 90% EtOAc/Hex) afforded 7.5 mg (57%) of 22L.

Step 3. Elimination of β-hydroxy ketone to enone 23L.

A mixture of the product from step 2 (22L, 7.5 mg, 0.015 mmol) and acetic acid/THF/$H_2O$ (2:1:1, 1.0 mL) was heated at 70° C. overnight. The reaction was cooled to rt, saturated aqueous $NaHCO_3$ (7 mL) was added and the mixture was extracted with EtOAc (2×6 mL). The combined organic phase was washed with brine (5 mL), dried ($Na_2SO_4$), filtered and concentrated in vacuo. Purification of the resulting residue by preparative thin layer chromatography (silica, 50% EtOAc/Hex) afforded 5.0 mg (69%) of 23L.

Step 4. Conversion of ester to acid 24L

The product of step 3 was then converted to the title product (24L) in accordance with the procedure in Example 1 (step 4B).

Human Recombinant $EP_4$ Receptor: Stable Transfectants.

Plasmids encoding the human $EP_4$ receptor were prepared by cloning the respective coding sequences into the eukaryotic expression vector pCEP4 (Invitrogen). The pCEP4 vector contains an Epstein Barr virus (EBV) origin of replication, which permits episomal replication in primate cell lines expressing EBV nuclear antigen (EBNA-1). It also contains a hygromycin resistance gene that is used for eukaryotic selection. The cells employed for stable transfection were human embryonic kidney cells (HEK-293) that were transfected with and express the EBNA-1 protein. These HEK-293-EBNA cells (Invitrogen) were grown in medium containing Geneticin (G418) to maintain expression of the EBNA-1 protein. HEK-293 cells were grown in DMEM with 10% fetal bovine serum (FBS), 250 μg ml$^{-1}$ G418 (Life Technologies) and 200 μg ml$^{-1}$ gentamicin or penicillin/streptomycin. Selection of stable transfectants was achieved with 200 μg ml$^{-1}$ hygromycin, the optimal concentration being determined by previous hygromycin kill curve studies.

For transfection, the cells were grown to 50–60% confluency on 10 cm plates. The plasmid pCEP4 incorporating cDNA inserts for the respective human prostanoid receptor (20 μg) was added to 500 μl of 250 mM $CaCl_2$. HEPES buffered saline×2 (2×HBS, 280 mM NaCl, 20 mM HEPES acid, 1.5 mM $Na_2HPO_4$, pH 7.05–7.12) was then added dropwise to a total of 500 μl, with continuous vortexing at room temperature. After 30 min, 9 ml DMEM were added to the mixture. The DNA/DMEM/calcium phosphate mixture was then added to the cells, which had been previously rinsed with 10 ml PBS. The cells were then incubated for 5 hr at 37° C. in humidified 95% air/5% $CO_2$. The calcium phosphate solution was then removed and the cells were treated with 10% glycerol in DMEM for 2 min. The glycerol solution was then replaced by DMEM with 10% FBS. The cells were incubated overnight and the medium was replaced by DMEM/10% FBS containing 250 μg ml$^{-1}$ G418 and penicillin/streptomycin. The following day hygromycin B was added to a final concentration of 200 μg ml$^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use.

Certain of the above compounds were tested for activity in the recombinant human $EP_4$ receptor assay described above and the results are reported in Table 1, below.

TABLE 1

| Example # | Structure | Comment | Binding Data (IC50 in nM) hEP4 | Functional Data (EC50 in nM) hEP4 |
|---|---|---|---|---|
| 2 | | low Rf | 100 | 11 |

TABLE 1-continued

| Example # | Structure | Comment | Binding Data (IC50 in nM) hEP4 | Functional Data (EC50 in nM) hEP4 |
|---|---|---|---|---|
| 1 | | low Rf | 400 | 67 |
| 1 | | high Rf | 200 | 136 |
| 3 | | low Rf | 1300 | 168 |
| 4 | | low Rf | 1000 | 214 |

TABLE 1-continued

| Example # | Structure | Comment | Binding Data (IC50 in nM) hEP4 | Functional Data (EC50 in nM) hEP4 |
|---|---|---|---|---|
| 5 | | low Rf | 500 | 251 |
| 6 | | low Rf | 35 | 314 |
| 7 | | low Rf | 1500 | 358 |
| 8 | | high Rf | 3500 | 362 |
| 9 | | | 600 | 387 |

TABLE 1-continued

| Example # | Structure | Comment | Binding Data (IC50 in nM) hEP4 | Functional Data (EC50 in nM) hEP4 |
|---|---|---|---|---|
| 10 |  | low Rf | 1800 | 456 |

EP activity indicates that the compounds of this invention are useful in treating asthma, dysmenorrhea as well as glaucoma and lowering intraocular pressure.

Other potential therapeutic applications are in osteoporosis, constipation, renal disorders, sexual dysfunction, baldness and in disorder of immune regulation.

EP Receptor Agonists May be Useful for Prevention and/or Treatment of the Following Diseases:

acute hepatitis, asthma, bronchitis, burn, chronic obstructive respiratory diseases, Crohn's disease, digestive ulcer, glaucoma (and other diseases related to elevated intraocular pressure), hemophagous syndrome, hepatopathy, hypercytokinemia at dialysis, hypertension, immunological diseases (autoimmune diseases, organ transplantation, etc.), inflammation (such as rheumatoid arthritis), Kawasaki disease, liver injury, macrophage activation syndrome, myocardial ischemia, nephritis, nerve cell death, osteoporosis and diseases associated with bone disorders, premature birth, pulmonary emphysema, pulmonary fibrosis, pulmonary injury, renal failure, sepsis, sexual dysfunction, shock, sleep disorder, Still disease, stomatitis, systemic granuloma, systemic inflammatory syndrome, thrombosis and stroke, ulcerative colitis.

The compounds of the invention may also be useful in the treatment of various pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be formulated into an ointment containing about 0.10 to 10% of the active ingredient in a suitable base of, for example, white petrolatum, mineral oil and petrolatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules made of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as inders such as starch, paste using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. An ophthalmic solution comprising a therapeutically effective amount of a compound of formula I:

or a pharmaceutically acceptable salt thereof, in admixture with a non-toxic, ophthalmically acceptable liquid vehicle, packaged in a container suitable for metered application wherein the wavy segment represents an α or β bond, a dashed line represents the presence or absence of a bond, $R^1$ is H, $R^2$ is OH, $R^3$ is H;

W is O;

R is selected from the group consisting of $CO_2R^4$, $CONR^4_2$, $CH_2OR^4$, $CONR^4SO_2R^4$, and $P(O)(OR^4)$;

$R^4$ is selected from the group consisting of H, phenyl and lower alkyl having from one to six carbon atoms;

Y is a covalent bond or is selected from the group consisting of $CH_2$, O, S and N; and Z is benzo[b]thiophen-3-yl or 3-chloro-benzo[b]thiophen-2-yl.

2. The ophthalmic solution of claim 1 wherein said compound is a compound of Formula III 3. A compound represented by formula I:

wherein the wavy segment represents an α or β bond, a dashed line represents the presence or absence of a bond, $R^1$ is H, $R^2$ is OH, $R^3$ is H;

W is O;

R is selected from the group consisting of $CO_2R^4$, $CONR^4_2$, $CH_2OR^4$, $CONR^4SO_2R^4$, and $P(O)(OR^4)$;

$R^4$ is selected from the group consisting of H, phenyl and lower alkyl having from one to six carbon atoms;

Y is a covalent bond or is selected from the group consisting of $CH_2$, O, S and N; and Z is benzo[b]thiophen-3-yl or 3-chloro-benzo[b]thiophen-2-yl.

4. The compound of claim 3 wherein said compound is represented by formula II:

wherein the hatched segment represents an α bond and the solid triangle represents a β bond.

5. The solution of claim 2, wherein said compound is selected from the group consisting of (Z)-7-{(1R,2R)-2-[(E)-5-(3-Chloro-benzo[b]thiophen-2-yl)-3-hydroxy-pent-1-enyl]-6-oxo-cyclohexyl}-hept-5-enoic acid;

(Z)-7-{(1R,6R)-6-[(E)-5-(3-Chloro-benzo[b]thiophen-2-yl)-3-hydroxy-pent-1-enyl]-2-oxo-cyclohex-3-enyl}-hept-5-enoic acid;

(Z)-7-{(1R,2R,3R)-2-[(E)-5-(3-Chloro-benzo[b]thiophen-2-yl)-3-hydroxy-pent-1-enyl]-3-hydroxy-6-oxo-cyclohexyl}-hept-5-enoic acid;

7-[(1R,2R,3R)-2-((E)-4-Benzo[b]thiophen-3-yl-3-hydroxy-but-1-enyl)-3-hydroxy-6-oxo-cyclohexyl]-hept-5-ynoic acid;

(Z)-7-[(1R,2R,3R)-2-((E)-4-Benzo[b]thiophen-3-yl-3-hydroxy-but-1-enyl)-3-hydroxy-6-oxo-cyclohexyl]-hept-5-enoic acid; and (Z)-7-{(1R,2R,3R,6R)-6-Chloro-2-[(E)-5-(3-chloro-benzo[b]thiophen-2-yl)-3-hydroxy-pent-1-enyl]-3-hydroxy-cyclohexyl}-hept-5-enoic acid.

6. The compound of claim 4, selected from the group consisting of (Z)-7-{(1R,2R)-2-[(E)-5-(3-Chloro-benzo[b]thiophen-2-yl)-3-hydroxy-pent-1-enyl]-6-oxo-cyclohexyl}-hept-5-enoic acid;

(Z)-7-{(1R,6R)-6-[(E)-5-(3-Chloro-benzo[b]thiophen-2-yl)-3-hydroxy-pent-1-enyl]-2-oxo-cyclohex-3-enyl}-hept-5-enoic acid;

(Z)-7-{(1R,2R,3R)-2-[(E)-5-(3-Chloro-benzo[b]thiophen-2-yl)-3-hydroxy-pent-1-enyl]-3-hydroxy-6-oxo-cyclohexyl}-hept-5-enoic acid;

7-[(1R,2R,3R)-2-((E)-4-Benzo[b]thiophen-3-yl-3-hydroxy-but-1-enyl)-3-hydroxy-6-oxo-cyclohexyl]-hept-5-ynoic acid;

(Z)-7-[(1R,2R,3R)-2-((E)-4-Benzo[b]thiophen-3-yl-3-hydroxy-but-1-enyl)-3-hydroxy-6-oxo-cyclohexyl]-hept-5-enoic acid; and (Z)-7-{(1R,2R,3R,6R)-6-Chloro-2-[(E)-5-(3-chloro-benzo[b]thiophen-2-yl)-3-hydroxy-pent-1-enyl]-3-hydroxy-cyclohexyl}-hept-5-enoic acid.

* * * * *